(12) United States Patent
Nguyen et al.

(10) Patent No.: US 8,779,238 B2
(45) Date of Patent: Jul. 15, 2014

(54) FLORAL DIP METHOD FOR TRANSFORMATION OF CAMELINA

(75) Inventors: Thu Nguyen, Brier, WA (US); Xunjia Liu, Saskatoon, CA (US); Jay Derocher, Bothell, WA (US)

(73) Assignee: Global Clean Energy Holdings, Inc., Long Beach, CA (US)

( * ) Notice: Subject to any disclaimer, the term of this patent is extended or adjusted under 35 U.S.C. 154(b) by 648 days.

(21) Appl. No.: 12/933,827

(22) PCT Filed: Mar. 19, 2009

(86) PCT No.: PCT/US2009/037627
§ 371 (c)(1),
(2), (4) Date: Feb. 22, 2011

(87) PCT Pub. No.: WO2009/117555
PCT Pub. Date: Sep. 24, 2009

(65) Prior Publication Data
US 2011/0145950 A1  Jun. 16, 2011

Related U.S. Application Data

(60) Provisional application No. 61/038,551, filed on Mar. 21, 2008.

(51) Int. Cl.
*A01H 5/10* (2006.01)

(52) U.S. Cl.
USPC ......... 800/294; 800/306; 800/287; 435/320.1

(58) Field of Classification Search
None
See application file for complete search history.

(56) References Cited

U.S. PATENT DOCUMENTS

| 2004/0031076 | A1* | 2/2004 | Kuvshinov et al. | ........... 800/294 |
| 2004/0154051 | A1 | 8/2004 | Cade et al. | |
| 2008/0066198 | A1 | 3/2008 | Nilsson et al. | |

FOREIGN PATENT DOCUMENTS

WO   WO 2007/028979   3/2007

OTHER PUBLICATIONS

Desfeux et al. (Plant Physiology, Jul. 2000, vol. 123, pp. 895-904).*
Langridge et al. (Nucleic Acids Research, vol. 19, No. 24, p. 6954).*
Edwards et al. (Nucleic Acids Research, vol. 19, No. 6, p. 1349).*
Xue et al. (Plant Cell Rep (2003) 21:1088-1094).*
English summary of Office Action issued in the related Chilean Patent Application No. 709-2009, mailed on Sep. 2012.
English translation of Office Action issued in the related Eurasian Patent Application No. 201071114, mailed on Oct. 31, 2012.

Kiphati et al., "*Agrobacterium tumefaciens* fur Has Important Physiological Roles in Iron and Manganese Homeostasis, the oxidative Stress Response, and Full Virulence," *Appl Env Microbial*, Aug. 2007, 73(15):4760-4768.
Clough et al., "Floral Dip: A Simplified Method for *Agrobacterium*-mediated transformation for *Arabidopsis thaliana*", *Plant Journal*, 1998, 16(6):735-743.
Kitphati et al., "*Agrobacterium tumefaciens fur* Has Important Physiological Roles in Iron and Manganese Homeostasis, the Oxidative Stress Response, and Full Virulence", *Appl. Env. Microbio.*, Aug. 2007, 73(15):4760-4768.
Lu et al., "Generation of transgenic plants of a potential oilseed crop *Camelina sativa* by *Agrobacterium*-mediated transformation", *Plant Cell Rep*, Feb. 2008; 27(2):273-8. Epub Sep. 27, 2007.
International Search Report based on International Patent Application No. PCT/US2009/037627, mailed on Jun. 30, 2009.
Written Opinion of the International Searching Authority based on International Patent Application No. PCT/US2009/037627, mailed on Jun. 30, 2009.
Curtis et al., "Transgenic radish (*Raphanus sativus L. longipinnatus* Bailey) by floral-dip method—plant development and surfactant are important in optimizing transformation efficiency", Transgenic Research, 2001, 10(4): 363-371.
Veluti-Iambi et al., "The current status of plant transformation technologies", *Current Science*, Feb. 10, 2003, 84(3): 368-380.
Wang et al., "Development of a novel *Agrobacterium*-mediated transformation method to recover transgenic *Brassica napus* plants.", *Plant Cell Rep.*, Nov. 2003, 22(4):274-81. Epub Aug. 29, 2003.
Tried et al., "Transformation of *Medicago truncatula* via infiltration of seedlings or flowering plants with *Agrobacterium*", *The Plant Journal*, 2000, 22(6):531-541.
Chang et al., "Stable genetic transformation of *Arabidopsis thaliana* by *Agrobacterium* inoculation in planta", *The Plant Journal*, 1994, 5(4):551-558.
Feldmann et al., "*Agrobacterium*-mediated transformation of germinating seeds of *Arabidopsis thaliana*: A non-tissue culture approach", *Mol. Gen. Genet.* 1987, 208:1-9.
Liu et al., In Planta Transformation of Pakchoi (*Brassica campestris L. ssp. Chinesis*) by infiltration of adult plants with *Agrobacterium*. Proc. 3$^{rd}$ IS on Diversification of Vegetable Crops,1998, 187-192.
Bechtold et al., "In Planta *Agrobacterium*-Mediated Transformation of Adult *Arabidopsis thaliana* Plants by Vacuum Infiltration", Chapter 28 of Methods in Molecular Biology, 1998, vol. 82, Arabidopsis Protocols, 259-266.
Curtis "Production of Transgenic Crops by the Floral-dip Method", *Methods in Molecular Biology*, 2005, vol. 286, Transgenic Plants: Methods and Protocols, 103-109.
Qing et al., "Transformation of Pakchoi (*Brassica campestris L. ssp. Chinesis*) by *Agrobacterium* infiltration", *Molecular Breeding* 2000, 6:67-72.

(Continued)

*Primary Examiner* — David T Fox
*Assistant Examiner* — Jared Shapiro
(74) *Attorney, Agent, or Firm* — Saliwanchik, Lloyd & Eisenschenk

(57) ABSTRACT

The present invention provides methods for transforming *Camelina* plants. In particular, the present invention relates to transforming *Camelina sativa* plants through contacting the plants to a dipping solution comprising *Agrobacterium*, a sugar, and a nonionic surfactant. The methods do not require a vacuum filtration step. The present invention provides, for example, useful methods for developing transformation systems for *Camelina sativa* that can enable manipulation of its agronomic qualities.

20 Claims, No Drawings

(56) References Cited

OTHER PUBLICATIONS

Clough "Floral Dip", *Methods in Molecular Biology*, 2005, vol. 286, *Transgenic Plants: Methods and Protocols*, 91-101.
Bechtold et al., "In Planta *Agrobacterium*-Mediated Gene Transfer by Infiltration of Adult *Arabidopsis thaliana* Plants" *C. R. Acad. Sci. Paris, Sciences de la vie/life sciences*, 1993, 316: 1194-1199.
Liu et al., "*Camelina saliva* transformation by floral dip and simple large-scale screening of markerless transformants", *In vitro Cellular & Developmental Biology Animal*, Apr. 2008, 44(Suppl. 5):S35-S42.
European Search Report and Written Opinion based on related European Patent Application No. 09722413.3, mailed on Sep. 27, 2011.

* cited by examiner

SEQUENCE LISTING

```
<160> NUMBER OF SEQ ID NOS: 2

<210> SEQ ID NO 1
<211> LENGTH: 24
<212> TYPE: DNA
<213> ORGANISM: Artificial Sequence
<220> FEATURE:
<223> OTHER INFORMATION: ABI3 prF Primer

<400> SEQUENCE: 1
gacggcacga ggagacttat attt                                          24

<210> SEQ ID NO 2
<211> LENGTH: 24
<212> TYPE: DNA
<213> ORGANISM: Artificial Sequence
<220> FEATURE:
<223> OTHER INFORMATION: BnKRP stop Primer

<400> SEQUENCE: 2
tcactctgat aatttaaccc actc                                          24
```

FLORAL DIP METHOD FOR TRANSFORMATION OF CAMELINA

CROSS-REFERENCES TO RELATED APPLICATIONS

The present application is a U.S. National Stage Application of International Application No. PCT/US2009/037627, filed Mar. 19, 2009, which claims priority to U.S. Provisional Patent Application No. 61/038,551, filed Mar. 21, 2008, each of which is incorporated by reference herein in its entirety for all purposes.

BACKGROUND OF THE INVENTION

The ability to genetically transform a plant is useful for studying gene function, producing heterologous proteins, or conferring new properties to the plant such as increased yield or disease resistance. A number of different methods have been developed for introducing transgenes into plants (Veluthambi et al., *Current Science* 84:368-380, 2003). Generally, each method has three common elements: i) a DNA delivery system, ii) a selection system to differentiate transformed cells or plants from untransformed ones, and iii) a procedure to regenerate the transformed cells or plants. These methods can include in vitro *Agrobacterium*-mediated gene transfer (tissue culture), in planta *Agrobacterium*-mediated gene transfer, and physical methods such as microinjection, polyethylene glycol (PEG)-mediated transfer into protoplasts, electroporation of protoplasts, and microprojectile bombardment (biolistics) (Klein et al., *Nature* 327:70-73, 1987).

Physical methods can be used for certain transformations; however, these methods are limited. For example, in microprojectile, or particle, bombardment, DNA-coated gold particles are introduced into target cells via electric discharge particle acceleration or helium gas. Disadvantages, though, are high copy number and rearrangement of the transgene. Also, with particle bombardment, a tissue culture stage is still necessary, bringing with it the inevitable risk of having somaclonal variation.

Alternatively, in vitro *Agrobacterium*-mediated gene transfer involves the introduction of a transgene into appropriate plant tissue and regeneration of the tissue into a whole plant. This method has been widely and successfully used with many dicot and monocot crops. However, transformation by tissue culture can be time-consuming and generally very particular to the skills of the researcher performing the transformation. Furthermore, there are several variables that must be considered with this method, such as explant availability, identification of a large population of regenerable cells, accessibility of regenerable cells to *Agrobacterium* inoculation, and appropriate media and hormones that induce shoot and root regeneration. Since the regeneration of a plant from tissue culture relies upon a few transformed cells, the resulting plants will likely have somaclonal variation, the sum of genetic and epigenetic changes in the transgenic plant that was inherited from the parental cells (Karp, *Euphytica* 85:295-302, 1995; Larkin and Scowcroft, *Theor. Appl. Genet.* 60:197-214, 1981).

In contrast, in planta *Agrobacterium*-mediated gene transfer has advantages over tissue culture or particle bombardment. For example, in planta methods do not require performance by a specialist, and less equipment, labor and reagents are needed to obtain transformed plants. Also, in a given T1 hemizygous transformant, all cells are transgenic. Thus, there is minimal somaclonal variation as compared to that typically encountered with tissue culture (Labra et al., *Theor. Appl. Genet.* 109:1512-1518, 2004). In planta transformation was first shown with *Arabidopsis* by imbibing seeds with *Agrobacterium* (Feldmann and Marks, *Mol. Gen. Genet.* 208:1-9, 1987). Later, Bechtold et al. (Bechtold et al., *C. R. Acad. Sci. (Paris) Life Sci.* 316:1194-1199, 1993) demonstrated in planta *Agrobacterium*-mediated transformation of *Arabidopsis* using whole plants and vacuum infiltration as a means to increase the likelihood of getting *Agrobacterium* penetration into the plant (see also, Chang at al., *Plant J.* 5:551-558, 1994; Mollier et al., *C.R. Acad. Sci. (Paris) Life Sci.* 318:465-474, 1995; Bechtold and Pelletier, *Meth. Mol. Biol.* 82:259-266, 1998; Ye et al., *Plant J.* 19:249-257, 1999; Bechtold et al., *Genetics* 155:1875-1887, 2000). Vacuum infiltration methods have been used successfully in transforming, for example, pakchoi (*Brassica rapa* L. ssp. chinensis) (Liu at al., *Acta Hortic.* 467:187-193, 1998; Qing et al., *Mol. Breed.* 6:67-72, 2000), alfalfa (*Medicago truncatula*) (Trieu et al., *Plant J.* 22:531-541, 2000), *Camelina sativa* (Lu and Kang, *Plant Cell Rep.* 27:273-278, 2008, e-pub. September 2007) and *Brassica napus* (Wang et al., *Plant Cell Rep.* 22: 274-281, 2003). While transformation has been shown with these particular plant varieties, transformation efficiencies have varied widely. Moreover, the method has not worked for some of the varieties without taking certain, specific steps. For example, vacuum infiltration does not transform *Medicago truncatula* unless a vernalization treatment is included (Trieu et al., *Plant J.* 22:531-541, 2000).

More recently, a floral dip method has been developed as an improvement upon in planta *Agrobacterium*-mediated transformation of *Arabidopsis* (Clough and Bent, *Plant J.* 16:735-743, 1998; Clough, *Meth. Mol. Biol.* 286:91-101, 2005). In the typical floral dip method, a vacuum is no longer required for efficient infiltration of *Agrobacterium* into the plant. However, frequent multiple applications of dipping solution comprising *Agrobacterium* to *Arabidopsis* has been shown to be detrimental to plant health, particularly if the dip intervals are less than every fourth day. Only *Arabidopsis* and radish (*Raphanus sativus* L. longipinnatus Bailey) have been successfully transformed by use of a floral dip method (Clough and Bent, *Plant J.* 16:735-743, 1998; Curtis and Nam, *Trans. Res.* 10:363-371, 2001; Curtis et al., *Trans. Res.* 11:249-256, 2002; Curtis, *Meth. Mol. Biol.* 286:103-110, 2005). A floral dip method has not been found that worked successfully with *B. napus* (Wang et al., *Plant Cell Rep.* 22: 274-281, 2003), a crop whose flowers more closely resemble those of *Arabidopsis*. As such, floral dip methods have only been successful with *Arabidopsis* and radish, and the transformation technique has been unsuccessful where it has been tried with other plant varieties (Curtis and Nam, *Trans. Res.* 10:363-371, 2001). These results indicate that floral dip methods are unpredictable as not all plant varieties are transformed with known floral dip techniques. In addition, some plant varieties may be successfully transformed with one technique but not with another.

In light of the current state of plant transformation methods, there remains a need to develop methods that can be used successfully with additional plant varieties. For example, *Camelina sativa* is an alternative oilseed crop whose oil holds promise for use in industrial applications, nutrition, and biofuels. Thus, there would be value in developing transformation systems for this crop to enable manipulation of its agronomic qualities. A transformation system for *Camelina sativa* via tissue regeneration has been described (WO 02/38779 A1). In addition, Lu and Kang (*Plant Cell Rep.* 27:273-278, 2008, e-pub. September 2007) recently reported in planta *Agrobacterium*-mediated transformation of *Camelina* using a vacuum infiltration method. However, they were not able to obtain transformants by floral dip without vacuum infiltration. Therefore, despite these recently developed transformation systems for *Camelina sativa*, better and less complex techniques need to be explored.

Accordingly, the present invention provides methods of transforming *Camelina sativa* plants that offer unique advantages over currently existing techniques.

DESCRIPTION OF THE TEXT FILE SUBMITTED ELECTRONICALLY

The contents of the text file submitted electronically are incorporated herein by reference in their entirety: A computer readable format copy of the Sequence Listing (filename: TARG-009-01US_ST25.txt, date recorded: Feb. 22, 2011, file size 1 kilobyte).

BRIEF SUMMARY OF THE INVENTION

The present invention provides methods for transforming *Camelina* plants. In particular, the present invention relates to transforming *Camelina sativa* plants through contacting the plants to a dipping solution comprising *Agrobacterium*, a sugar, and a nonionic surfactant. The present invention provides, for example, useful methods for developing transformation systems for *Camelina sativa* that can enable manipulation of its agronomic qualities.

In typical embodiment, the present invention provides a method of transforming a *Camelina* plant comprising the steps of: i) contacting the *Camelina* plant with a transformation dipping solution comprising a sugar, a nonionic surfactant, and an *Agrobacterium* comprising an expression vector; ii) removing the plant from the transformation dipping solution; iii) incubating the dipped plant following the first contacting step; iv) contacting the dipped plant with the transformation dipping solution; v) removing the dipped plant from the transformation dipping solution; vi) incubating the dipped plant following the second contacting step, and vii) selecting for a transformed *Camelina* plant. The method can include repeating steps i) through iii) after approximately one week and selecting the transformed *Camelina* plant. In a separate embodiment, the method of the invention can further comprise repeating steps i) through vi) after approximately one week and selecting the transformed *Camelina* plant.

In all embodiments of the present invention the method can comprise growing the plant in a controlled environment subsequent to contacting the plants with dipping solution. Typically, the plants of the invention are contacted with the transformation dipping solution for a duration of about 10 seconds to about 15 seconds to allow for permeation of the cell wall and transfer of the expression vector into the cytoplasm of the plant cells. The transformed plants comprising the *Agrobacterium* vector can be exposed to minimal sunlight. In addition, the *Camelina* plants can comprise buds, or flowers, or a combination thereof.

In certain embodiments of the invention, the *Agrobacterium*, for example, *Agrobacterium tumefaciens*, comprises at least one vector. In addition, where the vector is a binary vector, the vector can comprise a seed-specific promoter operatively associated with a gene-of-interest and a termination sequence. Typical embodiments of the method of the present invention comprises a vector with a plant-specific promoter operatively associated with a gene-of-interest and a termination sequence. In one embodiment of the method, the promoter is the cauliflower mosaic virus 35S promoter. The binary vector can be the pPZP200 vector in a particular embodiment. A selectable marker can be used in the vector of the invention.

The transformation dipping solution of the invention comprises a sugar, a non-ionic surfactant and an *Agrobacterium* vector. In a typical embodiment of the floral dip method, the sugar comprises sucrose or glucose at a concentration of from greater than about 0% to about 10%. In a specific embodiment of the invention the sugar is present at about 5%. The surfactant used in the method of the invention typically comprises a trisiloxane surfactant at a concentration of from greater than about 0% to about 0.5%. In a specific embodiment of the method, the trisiloxane surfactant is Silwet L-77® and is present at a concentration of about 0.025%. The transformation dipping solution can further comprise a phenolic compound, such as, for example, acetosyringone. The phenolic compound can be present in the dipping solution at a concentration of from greater than about 0 µM to about 500 µM. In a particularly useful embodiment of the invention the phenolic compound is present at about 300 µM.

DETAILED DESCRIPTION OF THE INVENTION

The present invention provides methods for transforming *Camelina* plants. In particular, the present invention relates to transforming *Camelina sativa* plants through contacting the plants to a dipping solution comprising *Agrobacterium*, a sugar, and a nonionic surfactant. The present invention provides, for example, useful methods for developing transformation systems for *Camelina sativa* that can enable manipulation of its agronomic qualities.

Transformation Dipping Solution:

As disclosed herein, the transformation dipping solution used in the present invention can include a sugar, a nonionic surfactant, and *Agrobacterium* comprising an expression vector. In certain embodiments, the transformation dipping solution can further include an agent to increase cell wall permeability, for example, a phenolic compound, such as acetosyringone. In particular embodiments, the transformation dipping solution at each dipping cycle can be the same initial solution or may be prepared fresh for each individual dipping or dipping cycle. The dipping solution is substantially composed of an aqueous solution.

The term "sugar" refers generally to a saccharide, disaccharide, or polysaccharide. Examples of a monosaccharide useful in the methods of the present invention can include, but are not limited to, glucose (dextrose), fructose, galactose, xylose, and ribose. A disaccharide useful in the methods of the present invention can include, by way of example, sucrose and lactose. In a particular embodiment of the present invention, the transformation dipping solution comprises sucrose. In some embodiments, the dipping solution can comprise greater than about 0 percent sugar by weight. Typically, the transformation dipping solution can comprise about 2% sugar and in certain embodiments, the dipping solution can comprise about 5% sucrose, or more.

The term "nonionic surfactant" refers generally to a non-ionic surfactant capable of assisting in the attachment of *A. tumefaciens* to the surface of the plant cell and thereby increasing transformation of *Camelina* plants (Opabode, *Biotech. Mol. Biol. Rev.* 1:12-20, 2006). In a typical embodiment, the nonionic surfactant used can include a trisiloxane surfactant, such as, for example, Silwet L-77®. Silwet L-77® is a mixture of about 84% polyalkyleneoxide modified heptamethyltrisiloxane (CAS#27306-78-1) and about 16% allyloxypolyethyleneglycol methyl ether (CAS#27252-80-8). The transformation dipping solution can comprise a percent by volume of surfactant greater than about 0%. The dipping solution can comprise up to about 0.05% surfactant, such as a trisiloxane surfactant. Generally, the amount of surfactant can be increased up to the point where the plants begin to show adverse effects. In certain embodiments, the trisiloxane surfactant, Silwet L-77®, can be present at about 0.025%.

The term "phenolic compound" refers generally to a molecule having a hydroxyl group attached to an aromatic hydrocarbon group. The phenolic compound is added to the transformation dipping solution to increase transformation efficiency due to activation of vir gene in *A. tumefaciens*. In certain embodiments of the present invention, the phenolic compound is acetosyringone (1-(4-hydroxy-3,5-dimethoxyphenyl)-ethanone). The concentration of the phenolic compound used in the present invention can range from about 0 µM to about 500 µM, or more. In certain embodiments, acetosyringone (Gelvin, *Ann. Rev. Plant Physiol. Plant Mol. Biol.*, 51:223-256, 2000) was present in the transformation dipping solution at a concentration of approximately 300 µM.

Plants

*Camelina* is a genus of flowering plants belonging to the Brassicaceae family. *Camelina sativa* is a particular species of *Camelina* that is important historically and is a source of oil that can be used in, for example, biofuels and lubricants. The term "plant" includes, but is not limited to, whole plants, plant organs, (e.g., buds, siliques, leaves, stems, flowers, roots, and the like), seeds and plant cells (including tissue culture cells) and progeny of the same.

*Agrobacterium*

The methods of the present invention relate to introduction of DNA into cells of a *Camelina* plant. In particular, *Agrobacterium* is capable of transferring foreign DNA, e.g., gene(s) to, in one embodiment of the present invention *Camelina sativa* cells. *Agrobacterium* has the natural ability to insert a specific part of its Ti (tumor-inducing) plasmid, called T-DNA (transferred DNA), into the chromosomal DNA of host plant cells. Foreign DNA artificially introduced into T-DNA is inserted into the plant genome by this natural vector system. The present invention can be applied with a wide variety of binary vector systems comprising a T-DNA having a plant selectable marker gene under a promoter and promoter-gene-of-interest-terminator expression cassette. A large number of vectors are well known in the art and can be used in the methods of the present invention. In a particular embodiment, pPZP200 was used as the binary vector comprising the constitutive promoter CaMV 35S-BAR herbicide marker-terminator cassette in combination with a seed-specific promoter-gene-of-interest-terminator cassette. It is well understood by the skilled artisan that any promoter-gene of interest-terminator cassette can be used in combination with any promoter-selectable marker-terminator cassette or any other expression vector selectable marker system can by used in the methods of the present invention.

The *Agrobacterium* in the present invention is, typically, *Agrobacterium tumefaciens*, yet additional species can be used, such as *Agrobacterium rhizogenes* or any species useful for genetic transformation of plants to produce genetically modified plants. While any of the numerous available strains of *A. tumefaciens* can be used in the present invention, strains of EHA105, At503, LBA4404, GV3101 (pMP90), and the like can be typically used with only some variation in efficiency of transformation.

The term "vector" refers to a piece of DNA, typically double-stranded, which can have inserted into it a piece of foreign DNA. The vector or replicon can be for example, of plasmid or viral origin. Vectors comprise "replicon" polynucleotide sequences that facilitate the autonomous replication of the vector in a host cell. The term "replicon" in the context of this disclosure also includes polynucleotide sequence regions that target or otherwise facilitate the recombination of vector sequences into a host chromosome. In addition, while the foreign DNA can be inserted initially into, for example, a DNA virus vector, transformation of the viral vector DNA into a host cell can result in conversion of the viral DNA into a viral RNA vector molecule. Foreign DNA is defined as heterologous DNA, which is DNA not naturally found in the host cell, which, for example, replicates with the vector molecule, encodes a selectable or screenable marker or transgene. The vector is used to transport the foreign or heterologous DNA into a suitable host cell. Once in the host cell, the vector can replicate independently of or coincidental with the host chromosomal DNA, and several copies of the vector and its inserted DNA can be generated. Alternatively, the vector can target insertion of the foreign or heterologous DNA into a host chromosome. In addition, the vector can also comprise the necessary elements that permit transcription of the inserted DNA into an mRNA molecule or otherwise cause replication of the inserted DNA into multiple copies of RNA. Some expression vectors additionally contain sequence elements adjacent to the inserted DNA that allow translation of the mRNA into a protein molecule. Many molecules of mRNA and polypeptide encoded by the inserted DNA can thus be rapidly synthesized.

The term "transgene vector" refers to a vector that contains an inserted segment of DNA, the "transgene" that is transcribed into mRNA or replicated as a RNA within a host cell. The term "transgene" refers not only to that portion of inserted DNA that is converted into RNA, but also those portions of the vector that are necessary for the transcription or replication of the RNA. In addition, a transgene need not necessarily comprise a polynucleotide sequence that contains an open reading frame capable of producing a protein. In the present invention the transgene comprises the gene-of-interest. The actual gene is not critical to the methods of the present invention.

The terms "transformed" and "transformation" refer to the introduction of DNA into a cell. The terms "transformant" and "transgenic" refer to plant cells, plants, and the like that have been transformed or have undergone a transformation procedure. The introduced DNA is usually in the form of a vector containing an inserted piece of DNA. As above, the introduced DNA sequence or transgene can be from the same species as the host cell or from a different species from the host cell, or it may be a hybrid DNA sequence, containing some foreign DNA and some DNA derived from the host species.

The term "selectable marker gene" means a gene that is optionally used in plant transformation to, for example, protect the plant cells from a selective agent. Only those cells or plants that receive a functional transgene are capable of dividing or growing under conditions having a selective agent. Examples of selective agents can include, for example, antibiotics, such as spectinomycin, neomycin, kanamycin, paromomycin, gentamicin, and hygromycin. Other selectable marker genes can include genes encoding herbicide resistance such as Bar (resistance against BASTA® (glufosinate ammonium), or phosphinothricin (PPT)), acetolactate synthase (ALS, resistance against inhibitors such as sulfonylureas (SUs), imidazolinones (IMIs), triazolopyrimidines (TPs), pyrimidinyl oxybenzoates (POBs), and sulfonylamino carbonyl triazolinones that prevent the first step in the synthesis of the branched-chain amino acids), and metal resistance or sensitivity. "Marker-positive" refers to plants that have been transformed to include the selectable marker gene.

For example, PPT-resistant refers to plants that have been transformed with the Bar marker gene.

The term "terminator" refers to transcription termination sequences. Many such sequences are well known in the art. A typical construct also will have a polyA sequence operatively associated with the heterologous gene sequence.

Promoters suitable for use in the present invention can be used either from the same species of plant to be transformed or can be from a heterologous species. The promoters for use in the methods of the present invention can also comprise a chimeric promoter which can comprise a combination of promoters that have an expression profile in common with one or more of those described above.

A constitutive promoter is a promoter that is capable of directly or indirectly activating the transcription of one or more DNA sequences or genes in all tissues of a transgenic plant. Typically, a constitutive promoter such as the 35 S promoter of CaMV (Odell, *Nature* 313:810-812, 1985) is used. Other examples of constitutive promoters useful in plants include the rice actin promoter (Elroy et al., *Plant Cell* 2:163-171, 1990), maize HE histone (Lepetit et al., *Mol. Gen. Genet.* 231:276-285, 1992) and the like.

The CKI transgenes of the present invention can be expressed using a promoter such as the BCEA (*B. campestris* embryo) promoter which has been shown to direct high levels of expression in very early seed development (i.e., is transcribed before the napin promoter). This is a period prior to storage product accumulation but of rapid pigment biosynthesis in the *Brassica* seed (derived from Johnson-Flanagan et al., *J. Plant Physiol.* 136:180, 1989; Johnson-Flanagan et al., *Physiol. Plant* 81:301, 1991). Seed storage protein promoters have also been shown to direct a high level of expression in a seed-specific manner (Voelker et al., *Plant Cell* 1:95, 1989; Altenbach et al., *Plant Mol. Biol.* 13:513, 1989; Lee et al., *Proc. Natl. Acad. Sci. USA* 99:6181, 1991; Russell et al., *Transgenic Res.* 6:157-68, 1997). The napin promoter has been shown to direct oleosin gene expression in transgenic *Brassica*, such that oleosin accumulates to approximately 1% of the total seed protein (Lee et al., *Proc. Natl. Acad. Sci. USA* 99:6181, 1991). In choosing a promoter, it may be desirable to use a tissue-specific or developmentally regulated promoter that allows suppression or over expression in certain tissues without affecting expression in other tissues. "Tissue-specific promoter" refers to DNA regions that direct gene expression primarily in a specific tissue such as, e.g., roots, leaves, stems, pistils, anthers, flower petals, seed coat, seed nucleus, or epidermal layers. Transcription stimulators, enhancers or activators can be integrated into tissue-specific promoters to create a promoter with a high level of activity that retains tissue specificity. For instance, promoters utilized in over expression will preferably be tissue-specific. Over expression in the wrong tissue such as leaves, when attempting to over express in seed storage areas, could be deleterious. Particularly suitable promoters are those that allow for example seed-specific, root-specific, leaf-specific, fruit-specific expression, and the like. This can be especially useful since seeds, roots, leaves and fruit are of particular interest. Some promoters specific for different tissue types are already available or can be isolated by well-established techniques (see, e.g., U.S. Pat. Nos. 5,792,925; 5,783,393; 5,859,336; 5,866, 793; 5,898,096; and 5,929,302) and as further described below. Table 1 lists other embryo-specific promoters that can be used to practice the present invention.

TABLE 1

Embryo-Specific Promoters

| Promoter | Embryo | Endosperm | Timing | Reference |
|---|---|---|---|---|
| oleosin from *Arabidopsis* | strong, uniform | none | traces at heart, higher early- to late-cotyledonary stage | Al et al., Plant Mol. Biol. 25: 193-205, 1994. |
| USP from *Vicia faba* | strong, uniform | none | early not known, strong in late cot. | Baumlein et al., Mol. Gen. Genet. 225: 459-467, 1991. |
| Legumin from *Vicia faba* | strong, preferential in cotyledons | aleurone layer (late) | early not known, strong in late cot. | Baumlein et al., supra 1991. |
| Napin from *Brassica* | | ? | late | Kohno-Murase, Plant Mol. Biol. 26: 1115-1124, 1994 |
| Albumin S1 from *Arabidopsis* | in axis only | none | early- to late-cotyledonary stage | Guerche et al., Plant Cell 2: 469-478, 1990 |
| Albumin S2 | in axis and cotyledons | none | early- to late-cotyledonary stage | Guerche et al., supra, 1990. |

In particular, embodiments to the present invention, a seed-specific promoter that is particularly active during the development of the embryonic plant of an immature seed is of interest. Expression of a gene of interest early in seed development can be desirable. Of interest can be those promoter sequences that initiate expression in early phase-specific embryo development. An early phase-specific promoter is a promoter that initiates expression of a protein prior to day 7 after pollination (walking stick) in *Arabidopsis* or an equivalent stage in another plant species. Examples of early embryo promoter sequences of interest include a promoter for the amino acid permease gene (AAP1) (e.g., the AAP1 promoter from *Arabidopsis thaliana*), a promoter for the oleate 12-hydroxylase:desaturase gene (e.g., the promoter designated LFAH 12 from *Lesquerella fendleri*), a promoter for the 2S2 albumin gene (e.g., the 2S2 promoter from *Arabidopsis thaliana*), a fatty acid elongase gene promoter (FAE1) (e.g., the FAE1 promoter from *Arabidopsis thaliana*), and the leafy cotyledon gene promoter (LEC2) (e.g., the LEC2 promoter from *Arabidopsis thaliana*). The AAP1, LFAH12, 2S2, and FAE1 promoters are inactive in the earliest stage of embryo development. They become transcriptionally active at progressively later stages in development starting with AAP1 followed by LFAH12, 2S2, and then FAE1. All four promoters then remain active through later embryonic developmental stages. The LEC2 promoter has an inverse expression profile. It is active in very early embryo development and then its activity declines gradually through later stages. Other embryo-specific promoters of interest include the promoters from the following genes: Seedstick (Pinvopich et al., *Nature* 424:85-88, 2003), Fbp7 and Fbp11 (Petunia Seedstick) (Colombo et al., *Plant Cell.* 9:703-715, 1997), Banyuls (Devic, *Plant J.*, 19:387-398, 1999), ABI3 (Ng et al., *Plant. Mol. Biol.* 54:25-38, 2004), agl-15, Agl18 (Lehti-Shiu et al., *Plant Mol. Biol.* 58:89-107, 2005), Phe1 (Kohler, *Genes Develop.* 17:1540-1553, 2003), emb175 (Cushing et al., *Planta.* 221: 424-436, 2005), L11 (Kwong et al., *Plant Cell* 15:5-18, 2003), Lec1 (Lotan, *Cell* 93:1195-1205, 1998), Fusca3 (Kroj et al., *Development* 130:6065-6073, 2003), TT12 (Debeaujon et al., *Plant Cell* 13:853-871, 2001), TT16 (Nesi et al., *Plant Cell* 14:2463-2479, 2002), A-RZf (Zou and Taylor, *Gene* 196:291-295, 1997), TTG1 (Walker et al., *Plant Cell* 11:1337-1350, 1999), TT1 (Sagasser et al., *Genes Dev.* 16:138-149, 2002), TT8 (Nesi et al., *Plant Cell* 12:1863-1878, 2000), and Gea-8 (carrot) (Lin et al., *J. Exp. Botany* 50:1139-1147, 1999) promoters. Embryo-specific promoters from monocots include Globulin, Knox (rice) (Postma-Haarsma, *Plant Mol. Biol.* 39:257-271, 1999), Oleosin (Plant, *Plant Mol. Biol.* 25:193-205, 1994; Keddie, *Plant Mol. Biol.* 24:327-340, 1994), Peroxiredoxin (Peri) (Haslekas et al., *Plant Mol. Biol.* 36:833-845, 1998), Haslekas et al., *Plant Mol. Biol.* 53:313-326, 2003), HvGAMYB (Diaz et al., *Plant J.* 29:453-464, 2002) and SAD1 (Isabel-LaMoneda et al, *Plant J.* 33:329-340, 1999) from Barley, and *Zea maize* Hybrid proline rich protein promoters (Jose-Estanyol et al., *Plant Cell* 4:413-423, 1992; Jose-Estanyol et al., *Gene* 356: 146-152, 2005).

Promoters of seed storage proteins are also of particular interest. The seed storage proteins are strictly regulated, being expressed almost exclusively in seeds in a highly tissue-specific and stage-specific manner (Higgins et al., *Ann. Rev. Plant Physiol.* 35:191-221, 1984; Goldberg et al., *Cell* 56:149-160, 1989). Moreover, different seed storage proteins may be expressed at different stages of seed development. Expression of seed-specific genes has been studied in great detail (see reviews by Goldberg et al., supra, and Higgins et al., supra). Examples of seed-specific promoters include LFAH12 of *Arabidopsis* and other plants, and the 5' regulatory regions of an *Arabidopsis* oleosin gene as described in U.S. Pat. No. 5,977,436 to Thomas et al. (incorporated in its entirety by reference), which when operably linked to either the coding sequence of a heterologous gene or sequence complementary to a native plant gene, direct expression of the heterologous gene or complementary sequence in a plant seed.

Suitable seed storage protein promoters for dicotyledonous plants include, for example, bean β-phaseolin, lectin, and phytohemagglutinin promoters (Sengupta-Gopalan, et al., *Proc. Natl. Acad. Sci. U.S.A.* 82:3320-3324, 1985; Hoffman et al., *Plant Mol. Biol.* 11:717-729, 1988; Voelker et al., *EMBO J.* 6:3571-3577, 1987); rapeseed (Canola) napin promoter (Radke et al., *Theor. Appl. Genet.* 75:685-694, 1988); soybean glycinin and conglycinin promoters (Chen et al., *EMBO J.* 7:297-302, 1988; Nielson et al., *Plant Cell* 1:313-328, 1989, Harada et al., *Plant Cell* 1:415-425, 1989; Beachy et al., *EMBO J.* 4:3047-3053, 1985); soybean lectin promoter (Okamuro et al., *Proc. Natl. Acad. Sci. USA* 83:8240-8244, 1986); soybean Kunitz trypsin inhibitor promoter (Perez-Grau et al., *Plant Cell* 1:1095-1109, 1989; Jofuku et al., *Plant Cell* 1:1079-1093, 1989); potato patatin promoter (Rocha-Sosa et al., *EMBO J.* 8:23-29, 1989); pea convicilin, vicilin, and legumin promoters (Rerie et al., *Mol. Gen. Genet.* 259: 148-157, 1991; Newbigin et al., *Planta* 180:461-470, 1990; Higgins et al., *Plant Mol. Biol.* 11:683-695, 1988; Shirsat et al., *Mol. Gen. Genetics* 215:326-331, 1989); and sweet potato sporamin promoter (Hattori et al., *Plant Mol. Biol.* 14:595-604, 1990).

For monocotyledonous plants, seed storage protein promoters useful in the practice of the invention include, e.g., maize zein promoters (Schernthaner et al., *EMBO J.* 7:1249-1255, 1988; Hoffman et al., *EMBO J.* 6:3213-3221, 1987 (maize 15 kD zein)); maize 18 kD oleosin promoter (Lee et al., *Proc. Natl. Acad. Sci. USA* 888:6181-6185, 1991); waxy promoter; shrunken-1 promoter; globulin 1 promoter; shrunken-2 promoter; rice glutelin promoter; barley hordein promoter (Marris et al., *Plant Mol. Biol.* 10:359-366, 1988); RP5 (Su et al., *J. Plant Physiol.* 158:247-254, 2001); EBE1 and 2 maize promoters (Magnard et al., *Plant Mol. Biol.* 53:821-836, 2003) and wheat glutenin and gliadin promoters (U.S. Pat. No. 5,650,558; Colot et al., *EMBO J.* 6:3559-3564, 1987).

Also suitable for practice of the present invention are promoters of genes for *B. napus* isocitratelyase and malate synthase (Comai et al., *Plant Cell* 1:293-300, 1989); delta-9 desaturase from safflower (Thompson et al., *Proc. Natl. Acad. Sci. USA* 88:2578-2582, 1991) and castor (Shanklin et al., *Proc. Natl. Acad. Sci. USA* 88:2510-2514, 1991); acyl carrier protein (ACP) from *Arabidopsis* (Post-Beittenmiller et al., *Nucl. Acids Res.* 17:1777, 1989), *B. napus* (Safford et al., *Eur. J. Biochem.* 174:287-295, 1988), and *B. campestris* (Rose et al., *Nucl. Acids Res.* 15:7197, 1987); β-ketoacyl-ACP synthetase from barley (Siggaard-Andersen et al., *Proc. Natl. Acad. Sci. USA* 88:4114-4118, 1991); and oleosin from *Zea mays* (Lee et al., *Proc. Natl. Acad. Sci. USA* 88:6181-6185, 1991), soybean (Genbank Accession No. X60773) and *B. napus* (Lee et al., *Plant Physiol.* 96:1395-1397, 1991).

Other promoters useful in the practice of the invention are known to those of skill in the art. Moreover, known methods can be used to isolate additional promoters suitable for use in accordance with the present invention. For example, differential screening techniques can be used to isolate promoters expressed at specific (developmental) times, such as during fruit development.

Promoters of seed-specific genes operably linked to heterologous coding sequences in chimeric gene constructs also maintain their temporal and spatial expression pattern in transgenic plants. Such examples include use of *Arabidopsis thaliana* 2S seed storage protein gene promoter to express enkephalin peptides in *Arabidopsis* and *B. napus* seeds (Vandekerckhove et al., *Bio/Technology* 7:929-932, 1989), bean lectin and bean β-phaseolin promoters to express luciferase (Riggs et al., *Plant Sci.* 63:47-57, 1989), and wheat glutenin promoters to express chloramphenicol acetyl transferase (Colot et al., supra). Such chimeric genes can be transferred into host plants either together in a single expression vector or sequentially using more than one vector.

In particular embodiments, the CaMV 35S promoter and the *Mirabilis mosaic* virus subgenomic transcript 9 promoter (MMVspt9pr) were used in the transformation method of the present invention. It should be noted that the specific promoters described above are only representative promoters that can be used in the methods of the present invention. Methods for identifying and characterizing promoter regions in plant genomic DNA and viral DNA are well known to the skilled artisan and include, for example, those described by Jordano et al., *Plant Cell* 1:855-866, 1989; Bustos et al., *Plant Cell* 1:839-854, 1989; Green et al., *EMBO J.* 7:4035-4044, 1988;

Meier et al., *Plant Cell* 3:309-316, 1991; and Zhang et al., *Plant Physiol.* 110:1069-1079, 1996.

In addition, enhancers are often required or helpful to increase expression of the gene of interest. It is necessary that these elements be operably linked to the sequence that encodes the desired proteins and that the regulatory elements are operable. Enhancers or enhancer-like elements may be either the native or chimeric nucleic acid fragments. This would include viral enhancers such as that found in the 35S promoter (Odell et al., *Plant Mol. Biol.* 10:263-272, 1988), enhancers from the opine genes (Fromm et al., *Plant Cell* 1:977-984, 1989), or enhancers from any other source that result in increased transcription when placed into a promoter operably linked to a gene of interest. For example, a construct can include the CaMV 35S promoter with dual transcriptional enhancer linked to the Tobacco Etch Virus (TEV) 5' nontranslated leader. The TEV leader acts as a translational enhancer to increase the amount of protein made.

Transformation of Plants

The methods of the present invention relate to transforming whole (intact) plants through an *Agrobacterium*-mediated procedure comprising dipping *Camelina sativa* plants into a solution having an *Agrobacterium* comprising the heterologous gene and a selectable marker as described above, a sugar, and a nonionic surfactant. The methods described herein can include, for example, more than one dipping cycle, wherein a dipping cycle includes at least one contacting step. A contacting step refers to dipping the plants into the solution and then removing the plants. In certain embodiments, a contacting step can include gently agitating the plants in the dipping solution for a period of time. In certain embodiments, contacting with agitation can comprise approximately 10 to 15 seconds. In certain embodiments of the present invention, a dipping cycle can include a first contacting step that is followed by a second contacting step. In some embodiments, the time between a first and a second contacting step can, for example, be about 24 to 48 hours. In certain embodiments, a dipping cycle can include only one contacting step. In some embodiments, the time between a first and a second dipping cycle can be, for example, about a week. The methods of the present invention can encompass several variations with the number of contacting steps and dipping cycles. As an alternative, the methods of the present invention can also comprise spraying the dipping solution onto the floral clusters of the plants.

For example, in a particular embodiment, *Camelina sativa* plants underwent a first dipping cycle wherein the plants were contacted with the dipping solution, and then removed and incubated following the first contacting step. After approximately 24 to about 48 hours, the plants were again contacted with the dipping solution and again removed and incubated following the second contacting step. The plants were then transferred to a growth chamber. After approximately one week, the plants underwent a second dipping cycle wherein the plants were contacted with the dipping solution and then contacted again after approximately 24 to about 48 hours. Following this second dipping cycle, the plants were incubated for about a week. A third dipping cycle can also be performed by contacting the plants with the dipping solution, removing the plants, and incubating the plants for approximately 24 to about 48 hours. The plants were again contacted with the solution and then removed. Following the three dipping cycles, plants were then grown to render transformed plants, or transformants.

In an alternative embodiment, two dipping cycles were performed. In another alternative embodiment, a dipping cycle included only one contacting step and the plants were transformed through two dipping cycles approximately a week apart. In a particular embodiment, two dipping cycles included only one contacting step per cycle, wherein the third dipping cycle included two contacting steps. In each of these alternative embodiments *Camelina* plants were transformed, although at differing frequencies.

After completion of the dipping cycles, the dipped plants are typically grown under normal conditions and watering can be stopped as the seeds mature. Transformed seeds are then harvested, threshed and cleaned. In some embodiments, the plants are grown in a growth chamber. In a particular embodiment described herein, the conditions of the growth chamber were 16/8 hours (light/dark) at 25/18° C. and light intensity of 270 μm/m$^2$/s. The plants typically are grown for about 80 to about 90 days from seeding to harvesting. In certain embodiments, the plants can be grown under constant light (150 μm/m$^2$/s) at 25° C. for about 55 to about 65 days. Certain *Camelina* varieties are sensitive to constant light and may exhibit some symptoms of stress, such as developing leaves that appear water-soaked and/or contain white areas. With 20/4 hours (light/dark) and temperatures of 26/26° C. (light/dark), plants grow well and the period from seed-to-seed is about 65 to about 70 days. In certain embodiments, the plants can be grown under 16/8 hours (light/dark) at 28/28° C. and a light intensity of 310.5 μm/m$^2$/s. The selection of light/dark, temperature and light intensity is typically optimized for the selection system used. Methods for optimization are well known to the skilled artisan. In certain additional embodiments, plants can also be covered, such as with a plastic wrap, and, in some instances, exposed to minimal sunlight during incubation between contacting with dipping solution.

Various selectable or detectable markers can be incorporated into the chosen expression vector to allow identification and selection of transformed plants, or transformants. Many methods are available to identify transformed plants, including examples such as DNA sequencing and PCR (polymerase chain reaction), Southern blotting, RNA blotting, immunological methods for detection of a protein expressed from the vector, e.g., precipitated protein that mediates phosphinothricin resistance, or other proteins such as reporter genes β-glucuronidase (GUS), luciferase, green fluorescent protein (GFP), DsRed, β-galactosidase, chloramphenicol acetyltransferase (CAT), alkaline phosphatase, and the like (Harlow and Lane, Antibodies: A Laboratory Manual. Cold Spring Harbor Laboratory Press, Cold Spring Harbor, N.Y., 1988; Ausubel et al., "Current Protocols in Molecular Biology", Greene Publishing Associates, New York, 2007; Sambrook, et al., Molecular Cloning: A Laboratory Manual, Third Edition, Cold Spring Harbor Press, N.Y., 2001, each incorporated herein by reference).

The following examples are provided merely to illustrate various aspects of the invention and shall not be construed to limit the invention in any way.

EXAMPLES

Example 1

The following example provides a protocol developed for transformation of *Camelina sativa* by *Agrobacterium*-mediated floral dip. No vacuum infiltration step was required to successfully transfect an expression vector into the plant cells and seed precursors.

Plant Material.

Five *Camelina* seeds were planted in each of eighteen 3.5"×3.5" pots containing potting soil (Sunshine® #3 soil).

The pots were placed in a tray and the tray was placed in a growth chamber for seed germination and plant growth. The conditions of the growth chamber were 16/8 hours (light/dark) at 25/18° C. and a light intensity of 270 μm/m²/s. The plants took about 80 to about 90 days to proceed from seed to harvesting. The plants were watered with 0.15% 20-20-20 fertilizer by applying the fertilizer into the trays every 3 to 4 days or as needed. Plants were staked to prevent them from lodging. Healthy *Camelina* plants were grown until they flowered. To encourage proliferation of secondary bolts, the first bolt could be clipped off. Clipping typically delayed flowering by about 7 days.

*Agrobacterium* Vectors.

*Agrobacterium tumefaciens* strains EHA105, At503, and GV3101 (pMP90) were tested for transformation of *Camelina sativa*. Plasmid pPZP200 was used as the binary vector and contained a T-DNA carrying the BAR (phosphinothricin resistance) selectable marker gene under the control of the CaMV 35S promoter and a seed-specific promoter-gene-of-interest-terminator cassette. A plasmid comprising only the selectable marker gene under control of the CaMV 35S promoter was included as a control. In total, 5 different constructs were used: TG_CS#3, TG_CS#4, TG_CS#5, TG_CS#6, and TG_CS#12, all containing the BAR selectable marker driven by the CaMV 35S promoter but different seed-specific promoter-gene-of-interest-terminator cassettes. The genes of interest included, *Brassica napus* KRP1 dominant negative 3 coding sequence (BnKRP1 DN3 cds; see WO 2007/016319, incorporated herein by reference in its entirety), *Arabidopsis thaliana* REVOLUTA coding sequence (AtREVcds), and *Camelina sativa* harpin-binding protein inverted repeat (CsHrBP-IR). The terminator sequences included mas 3' UTR for the BnKRP1cds and the CsHrBP-IR and the *Arabidopsis* REV 3' UTR for the AtREVcds.

10 μL of stock *Agrobacterium tumefaciens* carrying the gene-of-interest and selectable marker on a binary vector was inoculated into 5 mL of lysogeny broth (LB) medium containing 30 mg/L rifampicin and 200 mg/L spectinomycin and cultured at about 28° C. overnight. The next day, 800 mL fresh LB medium containing the same antibiotics was inoculated with 2.5 mL of the 5 mL overnight *Agrobacterium* culture and grown overnight at about 28° C. An *Agrobacterium tumefaciens* culture of $OD_{600}$ 1.5 was used for transformation.

Plant Transformation.

The *Agrobacterium* culture was spun down and resuspended in 400 mL of 5% sucrose, 0.025% Silwet L-77® with or without 300 μM acetosyringone. Siliques were clipped from the plants. The first dipping cycle included a first contacting step, in which all buds and flowers were dipped in the *Agrobacterium* solution for about 10 to about 15 seconds with gentle agitation. A film of liquid coating on each plant was seen. The dipped plants were laid horizontally on trays and covered with plastic wrap for about 24 hours without exposure to excessive sunlight. After about 24 hours, a second contacting step was done and plants were covered for another 24 hours. The dipped plants were then moved to a growth chamber. Subsequently, after about one week, a second dipping cycle as described above was carried out. A third dipping cycle was carried out about one week after the second dipping cycle. In total, there were 6 contacting steps in the 3 dipping cycles, wherein each dipping cycle included two contacting steps. Dipped plants were grown normally and watering was stopped as seeds became mature. Seeds were harvested, threshed and cleaned.

Identification of $T_1$ Transformants.

*Camelina* $T_1$ transformants were identified by germinating $T_1$ seeds in the presence of 30 mg/L glufosinate-ammonium (PPT; DL-phosphinothricin) and 150 mg/L Timentin® (ticarcillin disodium and clavulanate potassium). Putative transformants were transplanted to soil and grown for further testing by polymerase chain reaction (PCR), Southern blot, or other molecular analysis to verify presence of the gene-of-interest. $T_1$ seeds were sterilized in a 50-mL tube or a flask with 70% bleach (Javex-5®) for about 15 minutes and then washed 3 to 5 times with dd$H_2O$. The seeds were shaken during sterilization and washing. The sterilized seeds were then poured into a sterilized Petri dish and dried until use. The seeds were placed on agar selection plates. Any extra remaining seeds were allowed to dry in the hood and planted later if necessary.

The selection plates containing seeds were wrapped and incubated at about 25° C. for germination and seedling growth. The putative transformants (PPT-resistant seedlings) were transplanted to soil 7 to 10 days after seed plating. PPT-resistant seedlings had dark green cotyledons and were tall with long roots. These plants would continue to grow and produce true leaves. A few short dark green seedlings were also seen which grew slowly during the first several days on PPT medium but then eventually grew well and developed true leaves. PPT-sensitive seedlings were recognized by having pale green cotyledons and roots with few root hairs, and they were short in height, stunted in growth, and gradually died without producing true leaves. The numbers of PPT-resistant and PPT-sensitive seedlings were recorded for calculation of transformation efficiency. Tissue was collected from putative transformants for further testing by PCR, Southern blot or other molecular analysis to verify presence of the gene-of-interest.

Confirmation of Transgenic Seedlings by PCR.

Putative $T_1$ transformants were typed by PCR to confirm the presence of the transgene. Young $T_1$ leaf tissue from $T_1$ transformants was collected and genomic DNA was prepared by a cetyl trimethyl ammonium bromide (CTAB) protocol (Saghai-Maroof et al., *Proc. Nat'l. Acad. Sci. USA* 81:8014-8018, 1984). PCR primers specific to the promoter and gene-of-interest in the transferred T-DNA were used in the amplification reaction. The PCR reaction used 10 μL 2× Mango® mix (Taq DNA Polymerase, Bioline, London, UK), 0.8 μL each of 5 μM forward and reverse primers, and 7.4 μL of water to a final volume of 20 μL. One μL of CTAB-prepared DNA was used in each 20 μL reaction. Amplification conditions were the following: initial denaturation at 94° C. for 2 min, 32 cycles of 94° C. for 30 sec, 58° C. for 30 sec, 72° C. 1 min, and a final extension at 72° C. for 7 min. PCR products were run by electrophoresis on an 0.8% agarose gel and stained with ethidium bromide for visualization.

Determination of transgene insert number for a given $T_1$ transformant. Forty or eighty $T_2$ seeds harvested from each individual $T_1$ plant were put into a 2-mL tube for sterilization. One mL of 70% bleach (Javex-5®) was added to each tube and the tube shaken for 15 minutes. The sterilized seeds were rinsed with dd$H_2O$ and the rinsed seeds were plated onto an agar PPT plate (30 mg/mL). The plate was wrapped and incubated at 25° C. for germination and seedling growth. The numbers of PPT-resistant and PPT-sensitive seedlings were recorded about 7 to 10 days after plating. The insertion number for each $T_1$ transformant was calculated according to the law of Mendelian segregation.

Example 2

A number of variables were investigated in the transformation protocol for *Camelina sativa*, including, for example, the target tissues for dipping, the number and frequency of dippings, the *Agrobacterium* strain, the dilution of the *Agrobacterium*, the use of acetosyringone, and the method of introducing the *Agrobacterium* into the plant.

Dipping of buds only, flowers only, or both buds and flowers. *C. sativa* cv. Celine plants were planted for transformation as described in Example 1. Three scenarios were investigated to see if the target organs for dipping affected the transformation efficiency. When plants were at flowering stage, all flowers were clipped off (dip closed buds only), all closed buds were clipped off (dip open flowers only), or neither buds nor flowers were clipped off (dip both buds and flowers). Then plants were taken through the floral dip procedure as described in Example 1 using *Agrobacterium* At503 or EH105. Construct TG_CS#6 contained the BAR marker and Lec2pr-AtREV cds-REV 3' UTR cassette, and construct TG_CS#12 contained the BAR selectable marker and MMVsgt9pr-CsHrBP IR-mas 3' UTR/Lec2pr-AtREV cds-REV 3' UTR/Lec2pr-BnKRP1 DN3 cds-mas 3' UTR stack cassette. These transformations included a total of three dipping cycles, wherein the first two dipping cycles included only one contacting step per cycle and the third dipping cycle included two contacting steps. Selection of PPT-resistant $T_1$ transformants was as described in Example 1.

Table II shows the number of $T_1$ seeds screened, the number of $T_1$ PPT-resistant seedlings and the frequency of T1 PPT-resistant seedlings for each scenario. From these data, it was concluded that dipping both buds and flowers produced higher transformation efficiencies. In addition, *Agrobacterium* At503 appeared to provide a somewhat higher transformation efficiency than *Agrobacterium* EHA105 under these conditions.

Table III shows the number of $T_1$ seeds screened, the number of $T_1$ PPT-resistant seedlings and the frequency of $T_1$ PPT-resistant seedlings for each treatment. From these data, it was concluded that the use of acetosyringone was optional with undiluted *Agrobacterium* and did not improve the efficiency of transfection when the *Agrobacterium* was diluted to $OD_{600}$ 0.5. The *Agrobacterium* concentration did not play a significant role in transformation efficiency. In addition, three dipping cycles produced a higher transformation efficiency than two dipping cycles, although both methods produced a significant number of transformed plants (compare Tables II and III).

TABLE III

Results for floral dip with use of acetosyringone and *Agrobacterium* dilution

| Treatments | # seeds screened | $PPT^R T_1$ seedlings | % $PPT^R$ seedlings |
|---|---|---|---|
| C | 584 | 3 | 0.51 |
| D | 263 | 1 | 0.38 |
| E | 175 | 1 | 0.57 |
| F | 188 | 1 | 0.53 |

$PPT^R$ = PPT-resistant
Treatments:
C: *C. sativa* cv. Celine, At503/TG_CS#12, 5% sucrose, 0.025% Silwet L-77 ®, 0 µM acetosyringone, *Agrobacterium* diluted to O.D.$_{600}$ 0.5.
D: *C. sativa* cv. Celine, At503/TG_CS#12, 5% sucrose, 0.025% Silwet L-77 ®, 500 µM acetosyringone, *Agrobacterium* diluted to O.D.$_{600}$ 0.5.
E: *C. sativa* cv. Celine At503/TG_CS#12, 5% sucrose, 0.025% Silwet L-77 ®, 0 µM acetosyringone, no dilution of *Agrobacterium*.
F: *C. sativa* cv. Celine At503/TG_CS#12, 5% sucrose, 0.025% Silwet L-77 ®, 500 µM acetosyringone, no dilution of *Agrobacterium*.

TABLE II

Results for floral dip of different target tissues

| | Buds only | | | Flowers only | | | Buds and flowers | | |
|---|---|---|---|---|---|---|---|---|---|
| | # seeds screened | $PPT^R T_1$ seedlings | % $PPT^R$ | # seeds screened | $PPT^+ T_1$ seedlings | % $PPT^R$ | # seeds screened | $PPT^R T_1$ seedlings | % $PPT^R$ |
| A | 500 | 0 | 0 | 500 | 0 | 0 | 3400 | 31 | 0.91 |
| B | 450 | 0 | 0 | 500 | 0 | 0 | 640 | 5 | 0.78 |

$PPT^R$ = PPT-resistant
Treatments-
A: *C. sativa* cv. Celine, At503/TG CS#12, 5% sucrose, 0.025% Silwet L-77 ®.
B: *C. sativa* cv. Celine, EHA105/TG_CS#6, 5% sucrose, 0.025% Silwet L-77 ®.

Dipping with diluted or non-diluted *Agrobacterium*, use of acetosyringone and number of dippings. *C. sativa* cv. Celine plants were planted for transformation as described in Example 1. Studies were done to see if the concentration of *Agrobacterium* and the use of acetosyringone affected the transformation efficiency. When plants attained the flowering stage, both buds and flowers of plants were dipped using *Agrobacterium* At503. Construct TG_CS#12 comprises a BAR marker and MMVsgt9pr-CsHrBP IR-mas 3' UTR/Lec2pr-AtREV cds-REV 3' UTR/Lec2pr-BnKRP1 DN3 cds-mas 3' UTR stack cassette in its T-DNA. These transformations involved a total of two dipping cycles, wherein each dipping cycle included only one contacting step per cycle. Treatment C comprised At503 diluted to $OD_{600}$ 0.5 and no acetosyringone; treatment D comprised At503 diluted to $OD_{600}$ 0.5 and 500 µM of acetosyringone; treatment E comprised At503 undiluted and no acetosyringone; treatment F comprised At503 undiluted and 500 µM of acetosyringone. Selection of PPT-resistant $T_1$ transfottnants was carried out as described in Example 1.

Dipping with Different *Agrobacterium* Strains.

*C. sativa* cv. Celine plants were planted for transformation as described in Example 1. These studies were done to determine whether the strain of *Agrobacterium* affected the transformation efficiency and whether acetosyringone or *Agrobacterium* dilution would increase or decrease this efficiency. When plants attained the flowering stage, both buds and flowers of plants were dipped using *Agrobacterium* EHA105. Construct TG_CS#12 was used for the transformation and comprises a BAR marker and MMVsgt9pr-CsHrBP IR-mas 3' UTR/Lec2pr-AtREV cds-REV 3' UTR/Lec2pr-BnKRP1 DN3 cds-mas 3' UTR stack cassette in its T-DNA. These transformations involved a total of two dipping cycles, wherein each dipping cycle comprised only one contacting step. Treatment G comprised *Agrobacterium* EHA105 diluted to $OD_{600}$ 0.5 and no acetosyringone; treatment H comprised *Agrobacterium* EHA105 diluted to $OD_{600}$ 0.5 and 500 µM of acetosyringone; treatment I comprised *Agrobacterium* EHA105 undiluted and no acetosyringone; treatment J comprised *Agrobacterium* EHA105 undiluted and 500 of acetosyringone. Selection of PPT-resistant $T_1$ transformants was as described in Example 1.

Table IV shows the number of $T_1$ seeds screened, the number of $T_1$ PPT-resistant seedlings and the frequency of $T_1$ PPT-resistant seedlings for each treatment. From these data, it was concluded that *Agrobacterium* EHA105 was not as effective as the *Agrobacterium* At503 strain for *Camelina* transformation (compare Tables III and IV) and use of acetosyringone or *Agrobacterium* dilution did not increase the efficiency of transformation.

TABLE IV

Results for floral dip with EHA105/TG_CS#12

| Treatment | # seeds screened | $PPT^R T_1$ seedlings | % $PPT^R$ seedlings |
|---|---|---|---|
| G | 320 | 0 | 0 |
| H | 240 | 0 | 0 |
| I | 80 | 0 | 0 |
| J | 220 | 0 | 0 |

$PPT^R$ = PPT-resistant

Treatments -
G: *C. sativa* cv. Celine, EHA105/TG_CS#12, 5% sucrose, 0.025% Silwet L-77 ®, 0 μM acetosyringone, *Agrobacterium* diluted to $O.D._{600}$ 0.5.
H: *C. sativa* cv. Celine, EHA105/TG_CS #12, 5% sucrose, 0.025% Silwet L-77 ®, 500 μM acetosyringone, *Agrobacterium* diluted to $O.D._{600}$ 0.5.
I: *C. sativa* cv. Celine, EHA105/TG_CS #12, 5% sucrose, 0.025% Silwet L-77 ®, 0 μM acetosyringone, no dilution of *Agrobacterium*.
J: *C. sativa* cv. Celine, EHA105/TG_CS #12, 5% sucrose, 0.025% Silwet L-77 ®, 500 μM acetosyringone, no dilution of *Agrobacterium*.

Different methods of introducing *Agrobacterium* into *C. sativa*. An alternative method to introduce *Agrobacterium* into *Camelina*, called ovary injection, was investigated. Ovary injection is based on the idea that direct injection of *Agrobacterium* into the target tissue (ovaries) should help transformation efficiency. *C. sativa* cv. Celine plants were planted for transformation as described in Example 1. Closed buds and open flowers were injected at the carpels with an *Agrobacterium* suspension using a syringe attached with a small needle (gauge 27). The petals from closed buds were peeled back to ensure that carpels were being injected, in some instances. At least 500 buds and flowers were injected per treatment. Selection of marker-positive $T_1$ transformants was as described in Example 1.

Table V shows the number of $T_1$ seeds screened, the number of $T_1$ PPT-resistant seedlings and the frequency of $T_1$ PPT-resistant seedlings for each treatment. Treatments are described in Table VI. From these data, it was concluded that ovary injection was not an effective method for introducing *Agrobacterium* into *Camelina sativa* and varying the *Agrobacterium* strain, acetosyringone, *Agrobacterium* dilution, or Silwet L-77® did not improve the transformation efficiency.

The meristems of 20-day-old plants were also used for dipping. *C. sativa* cv. Celine plants were planted for transformation as described in Example 1. At 20 days, the tops of plants were dipped as described in Example 1. The idea behind this method was based upon the reasoning that if the meristematic cells were transformed, all seeds from flowers differentiated from these meristematic cells would be transgenic. Two $T_1$ transformants were PPT-resistant out of 600 seeds screened. One of these $T_1$ transformants died after transplantation due to fungal contamination. The other $T_1$ transformant survived and was confirmed as transgenic by PCR.

TABLE V

Results of *Camelina sativa* transformation by ovary injection

| Treatment | # seeds screened | $PPT^R T_1$ seedlings | % $PPT^R$ seedlings |
|---|---|---|---|
| 1 | 875 | 0 | 0 |
| 2 | 825 | 0 | 0 |
| 3 | 400 | 0 | 0 |
| 4 | 1000 | 0 | 0 |
| 5a | 200 | 0 | 0 |
| 5b | 600 | 0 | 0 |
| 5c | 900 | 0 | 0 |
| 6 | 430 | 0 | 0 |
| 7a | 450 | 0 | 0 |
| 7b | 500 | 0 | 0 |
| 7c | 770 | 0 | 0 |
| 8 | 750 | 0 | 0 |

$PPT^R$ = PPT-resistant

TABLE VI

Treatments for ovary injection

| Treatment | *Agrobacterium* strain/construct | Sucrose (%) | Dilution ($O.D._{600}$) of *Agrobacterium* | Silwet L-77 ® (%) | Acetosyringone (μM) |
|---|---|---|---|---|---|
| 1 | EHA105/TG_CS#6 | 5% | No dilution (1.7) | none | none |
| 2 | EHA105/TG_CS#6 | 5% | 0.5 | none | none |
| 3 | EHA105/TG_CS#6 | 5% | No dilution | none | 100 μM |
| 4 | EHA105/TG_CS#6 | 5% | 0.5 | none | 100 μM |
| 5a | EHA105/TG_CS#6 | 5% | No dilution | 0.025% | none |
| 5b | EHA105/TG_CS#12 | 5% | No dilution | 0.025% | none |
| 5c | At503/TG_CS#12 | 5% | No dilution | 0.025% | none |
| 6 | EHA105/TG_CS#6 | 5% | 0.5 | 0.025% | none |
| 7a | EHA105/TG_CS#6 | 5% | No dilution | 0.025% | 100 μM |
| 7b | EHA105/TG_CS#12 | 5% | No dilution | 0.025% | 100 μM |
| 7c | At503/TG_CS#12 | 5% | No dilution | 0.025% | 100 μM |
| 8 | EHA105/TG_CS#6 | 5% | 0.5 | 0.025% | 100 μM |

Example 3

*Camelina sativa* Celine and MT05, two different cultivars of *Camelina sativa*, were tested for transformation efficiency. Constructs.

Constructs TG_CS#3, TG_CS#4, TG_CS#5, and TG_CS#6 were transformed into *Agrobacterium* strain EHA105. All the constructs contained the BAR selectable marker driven by the CaMV 35S promoter but different seed-specific promoter-gene-of-interest-terminator cassettes within their T-DNAs. TG_CS#3 comprises the ABI3pr-At REV cds-At REV 3' UTR cassette; TG_CS#4 comprises the Lec2pr-BnKRP1 DN3 cds-mas 3' UTR cassette; TG_#5 comprises the ABI3pr-BnKRP1 DN3 cds-mas 3' UTR cassette; TG_#6 comprises the Lec2pr-At REV cds-REV 3' UTR cassette.

Seed Planting and Dipping.

*Camelina* seeds were planted every 7 to 15 days so that dipping could be staggered for the different constructs. Because MT05 flowered 7 days earlier than Celine, Celine was planted 7 days earlier than the seeds of cultivar MT05 so that both cultivars could be dipped with *Agrobacterium* containing the same construct at the same time. It was noted that MT05 did not grow as well as Celine in the growth chamber. The *Agrobacterium* was resuspended in 5% sucrose, 0.025% Silwet L-77® with or without 300 µM acetosyringone for dipping. The plants were subjected to a total of 6 contacting steps in the 3 dipping cycles, wherein each dipping cycle comprised two contacting steps and dipping cycles were at about 7 day intervals.

Transformant Identification.

MT05 and Celine $T_1$ seeds harvested from TG_CS#3, TG_CS#4, TG_CS#5, and TG_CS#6 dipped $T_0$ plants were selected on PPT selection medium. The PPT-resistant plants were further confirmed by PCR or other molecular analyses.

Table VII shows the number of $T_1$ seeds screened, the number of PPT-resistant seedlings, the number of PPT-resistant seedlings that were transgene-positive by molecular analyses, and the frequency of PPT-resistant or transgene-positive transformants for 2 *Camelina sativa* cultivars and 4 constructs. The discrepancy in the identification of transformants by selection on agar versus PCR or other molecular analyses may be due to a combination of factors, including some false-positive rate of identification using agar plates and some false-negative rate of identification using PCR or other molecular analyses. However, subsequent PCR or other molecular analyses on later generation plants have confirmed or eliminated each candidate $T_1$ transformant. These large-scale transformation data demonstrated that *Camelina sativa* cultivar Celine was about 5 to 10-fold better in transformation efficiency than MT05.

Plasmid Construction.

TG_CS#5, a binary plasmid, was constructed. This plasmid comprised the aadA gene (conferring spectinomycin resistance) for bacterium transformant selection and the BAR selectable marker gene for plant transformant selection. Along with the BAR marker cassette, the plasmid also harbored the ABI3pr-BnKRP1 DN3 cds-mas 3' UTR cassette between the left and right borders. This plasmid was transformed into *Agrobacterium tumefaciens* strain EHA105 by electroporation.

*Agrobacterium* Preparation.

Five mL of LB containing 30 mg/L rifampicin and 200 mg/L spectinomycin was inoculated with 10 µL of stock *Agrobacterium tumefaciens* strain EHA105 carrying TG_CS#5 and cultured overnight with shaking at about 28° C. 800 mL fresh LB containing the same antibiotics was then inoculated with 2.5 mL of the 5-mL *Agrobacterium* culture and cultured at about 28° C. overnight (until $OD_{600}$ was about 1.5). The *Agrobacterium* was spun down at 4500 rpm for 10 minutes and resuspended in 400 ml of 5% sucrose, 0.025% Silwet L-77® with or without 300 µM acetosyringone for dipping.

Dipping.

About 45 days after seeding, the Celine *Camelina* plants were flowering. Siliques from flowering plants were clipped and in the first dipping cycle, all buds and flowers were dipped in the *Agrobacterium* solution for about 10 to about 15 seconds with gentle agitation in a first contacting step. A film of liquid coating on the plants was seen. The dipped plants were laid horizontally on trays and covered with plastic wrap for about 24 hours without excessive sunlight. After about 24 hours, a second contacting step was done and the plants were covered for about another 24 hours. Then the plants were moved to a growth chamber. Over a period of about 2 weeks, a total of 6 contacting steps and 3 dipping cycles, were performed at about 7-day intervals.

TABLE VII

Transformation efficiency for 2 different *Camelina sativa* cultivars

| Cultivar | Construct | # $T_1$ seeds screened | # PPT-resistant[1] | # transgene-positive[2] | % PPT-resistant[3] | % transgene-positive[4] |
|---|---|---|---|---|---|---|
| MT05 | TG_CS#3 | 6000 | 16 | 2 | 0.267 | 0.033 |
|  | TG_CS#4 | 7300 | 29 | 8 | 0.397 | 0.110 |
|  | TG_CS#5 | 7800 | 42 | 6 | 0.538 | 0.077 |
|  | TG_CS#6 | 2000 | 1 | 1 | 0.050 | 0.050 |
| Celine | TG_CS#3 | 7000 | 69 | 37 | 0.986 | 0.529 |
|  | TG_CS#4 | 15400 | 56 | 34 | 0.364 | 0.221 |
|  | TG_CS#5 | 13275 | 161 | 67 | 1.213 | 0.505 |
|  | TG_CS#6 | 7600 | 29 | 10 | 0.382 | 0.132 |

[1]Number of $T_1$ seedlings identified as transformants by selection on PPT agar plates (30 mg/L).
[2]Number of PPT-resistant $T_1$ seedlings confirmed as transgene-positive by PCR or other molecular analyses.
[3]% PPT-resistant = (number of PPT-resistant $T_1$ seedlings/number of $T_1$ seeds screened) × 100.
[4]% transgene-positive = (number of transgene-positive $T_1$ seedlings/number of $T_1$ seeds screened) × 100.

Example 4

Plant Growth.

Five *Camelina* (cv. Celine) seeds were planted in each 3.5"×3.5" pot filled with Sunshine® #3 soil and eighteen pots were put in a tray. The trays were placed in a growth chamber in which about a 16-hour photoperiod with 270 µm/m²/s light intensity was provided. The temperatures were maintained at about 25° C. during light and about 18° C. during dark with natural humidity. Plants were watered with 0.15% 20-20-20 fertilizer every 3 to 4 days or when it was needed. Stakes were placed in corner pots and tape wrapped around the stakes to prevent plants from lodging.

Post-Dipping Management.

The dipped plants were grown normally in the growth chamber. Watering was stopped as seeds became mature. The mature dry seeds ($T_1$) were harvested, threshed and cleaned.

Identification of $T_1$ Transformants.

Identification of $T_1$ transformants was carried out by germinating $T_1$ seeds on PPT agar plates (30 mg/L). $T_1$ seeds were sterilized in a 50-mL tube or a flask with 70% bleach (Javex-5®) for about 15 minutes with shaking and then washed 3 to 5 times with ddH$_2$O. The sterilized seeds were then poured into a sterilized Petri dish and placed on selection plates. The remaining seeds were dried to be planted later if necessary. The selection plates were wrapped and placed at about 25° C. for germination and seedling growth.

Of 13275 seedlings screened, 161 grew on selection. The percentage of PPT-resistant seedlings was thus 1.21%. Each PPT-resistant seedling was transplanted into a 3.5 in.×3.5 in. pot containing Sunshine® #3 soil to obtain $T_2$ seeds for further confirmation of the transformant.

Confirmation of $T_1$ Transformants.

Leaf tissue was sampled from each individual transplanted $T_1$ plant. DNA was extracted using a CTAB protocol as described above. PCR was performed by amplifying with forward primer ABI3 prF: 5'-GAC GGC ACG AGG AGA CTT ATA TTT-3' (SEQ ID NO: 1) and reverse primer BnKRP stop: 5'-TCA CTC TGA TAA TTT AAC CCA CTC-3' (SEQ ID NO: 2) specific to the ABI3 promoter and the BnKRP1 cds, respectively. An expected 1.3-kb band was detected by gel electrophoresis for the PPT-resistant $T_1$ plants but not for wild-type untransformed controls. All PPT-resistant plants were confirmed by PCR. The transformation efficiency in this dipping transformation was about 1.2%.

Segregation analysis of $T_2$ seed to determine the number of transgene insertions. $T_1$ plants were bagged before flowering. $T_2$ seeds were harvested from each individual $T_1$ plant. Eighty (80) $T_2$ seeds were screened per T1 plant using the PPT selection, a process similar to the one described for $T_1$ seed screening above. Several segregation patterns were detected:
   a. 64 to 55 PPT-resistant to 16 to 25 PPT-sensitive, a ratio close to 3:1, indicating a single insertion of the transgene.
   b. 72 to 78 PPT-resistant to about 2 to 8 PPT-sensitive, a ratio close to 15:1, indicating 2 unlinked insertions of the transgene.
   c. All PPT-resistant, a ratio indicating more than 2 (multiple) insertions of the transgene.

About 40% of all transformants had a single insertion of the transgene.

$T_3$ Seed Analysis for Detection of Homozygous Progeny.

Twenty-four (24) $T_2$ seeds each from 20 single insertion events were planted and $T_2$ plants bagged before flowering. The $T_3$ seeds were harvested from each single plant and about 30 seed per plant were screened using PPT selection, a process similar to the one described for $T_1$ seed screening above. Null, homozygous and heterozygous $T_2$ plants could be identified from this $T_3$ seed analysis in the following manner:
   a. A 3:1 ratio of PPT-resistant: PPT-sensitive seedlings indicates that plant is heterozygous for the transgene;
   b. 100% PPT-resistant seedlings indicate the plant is homozygous for the transgene;
   c. 100% PPT-sensitive seedlings indicate the plant is null for the transgene.

Example 5

Transformation of *Camelina sativa* was investigated using additional cultivars in combination with different *Agrobacterium* strains. In addition, the effect on transformation efficiency of covering dipped plants with clear plastic versus black plastic was investigated.

Cultivars, *Agrobacteria* and Construct.

Cultivar lines CS3, CS6, CS32 and Celine were transformed with the following *Agrobacteria*: AT503, EHA105, and GV3101 (pMP90). The construct used was TG_CS#6, comprising the BAR marker driven by the CaMV35S promoter and the Lec2pr-AtREV cds-REV 3' UTR in an expression cassette.

Dippings.

Plants were grown and dipped as described in Example 1. After the first dip, the dipped plants were laid horizontally on trays and covered with either a clear plastic wrap (Saran®) or black plastic for about 48 hours without exposure to excessive sunlight. After about 48 hours, the dipped plants were then moved to a growth chamber. Subsequently, after about one week (7 days), a second dipping cycle was carried out and the plants covered with either clear plastic or black plastic again for about 48 hours before moving to a growth chamber. In total, there were 2 contacting steps in 2 dipping cycles, wherein each dipping cycle included one contacting step. Dipped plants were grown normally and watering was stopped as seeds became mature. Seeds were harvested, threshed and cleaned.

Transformant Identification.

Cultivar CS3, CS6, CS32 and Celine $T_1$ seeds harvested from TG_CS#6 dipped $T_0$ plants were selected on PPT selection medium (30 mg/L). The PPT-resistant plants were further confirmed by PCR or other molecular analyses.

Results and Conclusions.

Tables VIII and IX show the number of $T_1$ seeds screened in two separate screenings for each *Camelina sativa* cultivar line and *Agrobacterium*, the number of PPT-resistant seedlings, and the frequency of PPT-resistant transformants for 4 *Camelina sativa* cultivars, 3 *Agrobacteria* and 1 construct. From these data it was concluded that *Agrobacterium* strain AT503 gave the best transformation efficiency for all 4 *Camelina sativa* cultivars. Strain GV3101 (pMP90) only gave high efficiency transformation with just the Celine cultivar. *Agrobacterium* strain EHA105 may be used in transformation of any of the *Camelina sativa* cultivars, but the transformation efficiency is low.

TABLE VIII

The transformation efficiencies for 4 different *Camelina sativa* cultivars with 3 different *Agrobacteria* using a clear plastic (Saran ®) covering after dipping.

| | CS3 | | | CS6 | | | CS32 | | | Celine | | |
|---|---|---|---|---|---|---|---|---|---|---|---|---|
| | Seeds screened | PPT$^R$ | % efficiency | Seeds screened | PPT$^R$ | % efficiency | Seeds screened | PPT$^R$ | % efficiency | Seeds screened | PPT$^R$ | % efficiency |
| AT503#6 | 1000 | 12 | 1.2 | 1000 | 18 | 1.8 | 1000 | 12 | 1.2 | 1000 | 8 | 0.8 |
| | 229 | 0 | 0 | 1000 | 11 | 1.1 | 1000 | 15 | 1.5 | 1000 | 19 | 1.9 |
| EHA105#6 | 1000 | 4 | 0.4 | 1000 | 2 | 0.2 | 1000 | 0 | 0 | 1000 | 4 | 0.4 |
| | 1000 | 1 | 0.1 | 1000 | 1 | 0.1 | 1000 | 1 | 0.1 | 673 | 1 | 0.16 |

TABLE VIII-continued

The transformation efficiencies for 4 different *Camelina sativa* cultivars with 3 different *Agrobacteria* using a clear plastic (Saran ®) covering after dipping.

|  | CS3 | | | CS6 | | | CS32 | | | Celine | | |
|---|---|---|---|---|---|---|---|---|---|---|---|---|
|  | Seeds screened | PPT$^R$ | % efficiency | Seeds screened | PPT$^R$ | % efficiency | Seeds screened | PPT$^R$ | % efficiency | Seeds screened | PPT$^R$ | % efficiency |
| GV3101 (pMP90) #6 | 1000 | 0 | 0 | 1000 | 0 | 0 | 1000 | 1 | 0.1 | 1000 | 14 | 1.4 |
|  | 1000 | 0 | 0 | 1000 | 1 | 0.1 | 1000 | 0 | 0 | 1000 | 12 | 1.2 |

PPT$^R$ = number of seedlings that were PPT-resistant.
6 = TG_CS#6 construct (Lec2pr - AtREV cds - REV 3' UTR, BAR marker)

TABLE IX

The transformation efficiencies for 4 different *Camelina sativa* cultivars with 3 different *Agrobacteria* using black plastic covering after dipping.

|  | CS3 | | | CS6 | | | CS32 | | | Celine | | |
|---|---|---|---|---|---|---|---|---|---|---|---|---|
|  | Seeds screened | PPT$^R$ | % efficiency | Seeds screened | PPT$^R$ | % efficiency | Seeds screened | PPT$^R$ | % efficiency | Seeds screened | PPT$^R$ | % efficiency |
| AT503#6 | 1000 | 0 | 0 | 1000 | 2 | 0.2 | 1000 | 0 | 0 | 1000 | 15 | 1.5 |
| EHA105#6 | 1000 | 1 | 0.1 | 1000 | 0 | 0 | 1000 | 3 | 0.3 | 760 | 4 | 0.5 |
| GV3101 (pMP90) #6 | 1000 | 1 | 0.1 | 916 | 0 | 0 | 1000 | 1 | 0.1 | 1000 | 16 | 1.6 |

PPT$^R$ = number of seedlings that were PPT-resistant.
6 = TG_CS#6 construct (Lec2pr - AtREV cds - REV 3' UTR, BAR marker)

When black plastic was used as the covering after dipping, it was observed that strain AT503 now was only effective in transformation of Celine (Table IX). Strain GV3101 (pMP90) was again specifically compatible with Celine. As observed in the clear covering (Saran®) experiment (Table VIII), use of strain EHA105 for transformation of *Camelina sativa* gave low transformation efficiency.

Curiously, it appears these 4 *Camelina sativa* cultivars are not sensitive to light when they are transformed with strain GV3101 (pMP90) or strain EHA105. By contrast, 3 of the 4 cultivars (CS3, CS6 and CS32) were sensitive to light when AT503 was used for transformations. In other words, darkness had a negative effect in transformations of CS3, CS6 and CS32 with the *Agrobacterium* AT503 strain. These experiments may indicate that the transformation efficiency is dependent on interactions of the following: *Camelina sativa* cultivar, *Agrobacterium* strain and light.

Example 6

The following example provides a simple, efficient protocol for large-scale screening of transformants subsequent to floral dip. In a typical embodiment of the method, a plant of a *Camelina* species was transformed with an expression construct that does not comprise a selectable marker. Successful transformation was determined by a PCR-based method.

In this particular example, *Camelina sativa* cv. Celine was transformed with constructs bearing no selectable marker. A simple and efficient protocol for large-scale screening of markerless transformants was established that did not require any DNA extraction buffers or kits.

Cultivar, *Agrobacterium* and Constructs.

*Camelina* cultivar Celine was transformed with EHA105 carrying TG_CS#13, TG_CS#14, TG_CS#15, and TG_CS#16 as described in Example 1. TG_CS#13 has the Lec2pr-BnKRP1 DN3 cds-mas 3' UTR cassette; TG_CS#14 has the Lec2pr-AtREV cds-REV 3' UTR cassette; TG_CS#15 has the Lec2pr-AtREV cds-REV 3' UTR/Lec2pr-BnKRP1 DN3 cds-mas 3' UTR stack cassette; TG_CS#16 has the MMVsgt9pr-BnKRP1 DN3 cds-mas 3' UTR cassette.

PCR Screening.

A tray containing 288 cells (24 columns×12 rows) was used for seed planting. One $T_1$ seed was planted in each cell with Sunshine® #3 soil. The tray was placed onto a base tray filled with the same Sunshine® #3 soil so that the seedlings could be watered from below. The tray was covered with a clear plastic lid after planting and put at about 25° C. for germination or placed at about 4° C. for 2 to 3 days (for uniform germination if necessary) before moving to the 25° C. growth chamber. About 7 days after planting, or when the cotyledons were expanded, half of a cotyledon was cut from each seedling and pooled with 11 other seedlings (pools of 12 seedlings) in a TissueLyser (Qiagen) micro tube. About 100 to about 200 µL TE buffer (10 mM Tris, 1 mM EDTA pH 8.0) was added to each micro tube, and the tubes were capped and shaken for about 6 minutes at 20/s frequency with Tungsten Carbide Beads (3 mm) in a TissueLyser machine (Qiagen) to lyse the cells. The tubes were spun briefly after the shaking, so that aerosolization from opening the caps would be minimized to avoid cross contamination between tubes. About 30 µL ground tissue extract was spotted onto Whatman filter paper. 1 to 2 disk punches (2 mm) were used as template for PCR after the spots were dried. The dried spotted filter paper was saved for later use if necessary. PCR was performed with primers specific to the promoter (forward primer) and gene (reverse primer) of the transgene to identify putative transformants (As described above). A 96-well (8×12), 0.2-ml PCR microplate is recommended for large-scale PCR instead of individual PCR tubes. Mango® PCR mix (Bioline) or other alternative PCR mix was used for the PCR reactions. PCR was as described in Example 4.

Pools showing a band of the expected size in PCR were deconvoluted to identify the individual $T_1$ seedling(s) that was responsible for the positive band. A half-cotyledon from each seedling in the pool of interest was ground (TissueLyser, Qiagen) and taken through PCR as described above to find the positive transformant(s) in the pool of interest.

Putative transformants were transplanted into pots. Leaf tissue was collected when the plants were big enough and PCR was performed again to further confirm that a plant carried a given transgene. Confirmation of presence of the transgene was done by either conventional PCR (running out amplification products on agarose gels) or real-time PCR. Southern blots were done for putative transformants to determine single insertion events, and molecular analyses were done for expression of the transgene.

96 (PCR wells or pools)×12 seedlings/pool, or about 1152 seedlings can be screened in each PCR run. The sensitivity of the PCR could be improved with less than 12 samples per pool.

What is claimed is:

1. A method of transforming a *Camelina* plant comprising within a first dipping cycle,
   i) contacting the *Camelina* plant with a first transformation dipping solution comprising a sugar, a nonionic surfactant, and an *Agrobacterium* comprising a first expression vector capable of expression in the *Camelina* plant, wherein the contacting step comprises dipping the *Camelina* plant into the solution;
   ii) removing the plant from the first transformation dipping solution, thereby conducting a first contacting step to produce a first dipped plant;
   iii) incubating the first dipped plant;
   iv) in the same first dipping cycle, contacting the first dipped plant with a second transformation dipping solution comprising a sugar, a nonionic surfactant, and an *Agrobacterium* comprising a second expression vector capable of expression in the *Camelina* plant, thereby conducting a second contacting step to produce a twice dipped plant, wherein the contacting step comprises dipping the *Camelina* plant into the solution;
   v) removing the twice dipped plant from the second transformation dipping solution; and
   vi) incubating the twice dipped plant;
   wherein the sugar is a disaccharide, the nonionic surfactant is trisiloxane, and both flowers and buds are present during the dipping steps;
   wherein said method does not involve vacuum infiltration.

2. The method of claim 1 further comprising (vii) identifying whether or not the *Camelina* plant has been transformed.

3. The method of claim 1, wherein the time between the first dipping step and the second dipping step is 24 hours to 48 hours.

4. The method of claim 1, wherein the method further comprises repeating steps i) through iii) in a second dipping cycle starting approximately one week after conclusion of the first dipping cycle.

5. The method of claim 1, wherein the method further comprises repeating steps i) through vi) in a second dipping cycle starting approximately one week after conclusion of the first dipping cycle.

6. The method of claim 1, wherein the first and/or second dipping steps comprise a dipping duration of 10 seconds to 15 seconds.

7. The method of claim 1, wherein the first and second expression vectors are identical.

8. The method of claim 1, wherein the first and/or second expression vector is a binary vector comprising a seed-specific promoter operatively associated with a gene-of-interest and a termination sequence.

9. The method of claim 8, wherein the binary vector comprises pPZP200.

10. The method of claim 1, wherein the first and/or second expression vector comprises a plant-specific promoter operatively associated with a gene-of-interest and a termination sequence.

11. The method of claim 1, wherein the *Agrobacterium* in the first and/or second transformation dipping solution comprises *Agrobacterium tumefaciens*.

12. The method of claim 1, wherein the sugar in the first and/or second transformation dipping solution comprises sucrose.

13. The method of claim 1, wherein the sugar in the first and/or second transformation dipping solution is 0% to 10% by weight of the solution.

14. The method of claim 13, wherein the sugar is about 5% by weight of the solution.

15. The method of claim 1, wherein the nonionic surfactant in the first and/or second transformation dipping solution is between 0% to 0.5% by volume of the solution.

16. The method of claim 1, wherein the trisiloxane surfactant is about 0.025% by volume of the solution.

17. The method of claim 1, wherein the first and/or second transformation dipping solution further comprises acetosyringone.

18. The method of claim 17, wherein the concentration of acetosyringone is between 0 μM to 500 μM of the solution.

19. The method of claim 2, wherein the transformation efficiency is at least 0.1%.

20. The method of claim 1, wherein the *Camelina* plant is grown before and/or after the first dipping cycle under a condition selected from the group consisting of
   (1) 16/8 hours (light/dark) at 25° C./18° C. (light/dark) and light intensity of about 270 μm/m$^2$/s;
   (2) constant light of about 150 μm/m$^2$/s at 25° C.;
   (3) 20/4 hours (light/dark) at 26° C./26° C. (light/dark); and
   (4) 16/8 hours (light/dark) at 26° C./26° C. (light/dark) and light intensity of about 310 μm/m$^2$/s.

* * * * *

UNITED STATES PATENT AND TRADEMARK OFFICE
CERTIFICATE OF CORRECTION

PATENT NO.         : 8,779,238 B2                                        Page 1 of 1
APPLICATION NO.    : 12/933827
DATED              : July 15, 2014
INVENTOR(S)        : Thu Nguyen et al.

It is certified that error appears in the above-identified patent and that said Letters Patent is hereby corrected as shown below:

In the Specification

Column 9,
Line 27, "(Peri)" should read --(Per1)--.

Column 15,
Line 26, "frequency of T1" should read --frequency of $T_1$--.

Column 15,
Line 43, "At503/TG CS#12," should read --At503/TG_CS#12,--.

Column 15,
Line 66, "$T_1$ transfottnants" should read --$T_1$ transformants--.

Column 16,
Line 67, "and 500 of" should read --and 500 μM of--.

Signed and Sealed this
Ninth Day of December, 2014

Michelle K. Lee
*Deputy Director of the United States Patent and Trademark Office*